(12) United States Patent
Brudniok

(10) Patent No.: US 10,307,121 B2
(45) Date of Patent: Jun. 4, 2019

(54) X-RAY DEVICE HAVING AN ADJUSTING APPARATUS

(71) Applicant: KUKA Deutschland GmbH, Augsburg (DE)

(72) Inventor: Sven Brudniok, Langerringen (DE)

(73) Assignee: KUKA Deutschland GmbH, Augsburg (DE)

( * ) Notice: Subject to any disclaimer, the term of this patent is extended or adjusted under 35 U.S.C. 154(b) by 413 days.

(21) Appl. No.: 15/105,837

(22) PCT Filed: Dec. 3, 2014

(86) PCT No.: PCT/EP2014/076379
§ 371 (c)(1),
(2) Date: Sep. 15, 2016

(87) PCT Pub. No.: WO2015/090963
PCT Pub. Date: Jun. 25, 2015

(65) Prior Publication Data
US 2017/0188985 A1 Jul. 6, 2017

(30) Foreign Application Priority Data
Dec. 17, 2013 (DE) .......................... 10 2013 226 289

(51) Int. Cl.
*A61B 6/14* (2006.01)
*H05G 1/02* (2006.01)
*A61B 6/00* (2006.01)

(52) U.S. Cl.
CPC .......... *A61B 6/4441* (2013.01); *A61B 6/4452* (2013.01); *A61B 6/4458* (2013.01); *A61B 6/56* (2013.01)

(58) Field of Classification Search
CPC ... A61B 6/4441; A61B 6/4452; A61B 6/4458; A61B 6/56; A61B 2560/0406;
(Continued)

(56) References Cited

U.S. PATENT DOCUMENTS 6,325,537 B1 12/2001 Watanabe
6,466,641 B1 * 10/2002 Virta ......................... A61B 6/14
378/38

(Continued)

FOREIGN PATENT DOCUMENTS

CN 1818777 A 8/2006
DE 69831003 T2 1/2006
(Continued)

OTHER PUBLICATIONS

European Patent Office; Search Report and Written Opinion in International Patent Application No. PCT/EP2014/076379 dated Feb. 2, 2015; 11 pages.
(Continued)

*Primary Examiner* — Irakli Kiknadze
(74) *Attorney, Agent, or Firm* — Dorton & Willis, LLP

(57) ABSTRACT

An X-ray arrangement for a medical work station includes a frame having a first frame section supporting an X-ray transmitter and a second frame section opposite the first frame section and supporting an X-ray receiver. The medical work station further includes an adjustment device configured to change a relative pose of at least one of the X-ray transmitter or the X-ray receiver relative to the frame by adjusting at least one of the pose of the X-ray transmitter at the first frame section or the pose of the X-ray receiver (at the second frame section independently of one other. In one aspect, the frame may be shaped as a C-arm.

17 Claims, 9 Drawing Sheets

(58) Field of Classification Search
CPC .... A61B 2560/0437; A61B 2560/0443; A61B 50/26; A61B 6/035; A61B 6/4405; A61B 6/4429; A61B 6/587; A61B 6/4464; A61B 6/4014; A61B 6/027; A61B 6/0407; A61B 6/102; A61B 6/4482; A61B 6/4488; A61B 6/504; A61B 6/4291; H01L 2224/48091; H01L 2924/00014; H01L 2224/48247; H01L 2224/49107; H01L 2224/73265; A61G 13/0036; A61G 13/0054; A61G 13/04; A61G 13/06; A61G 13/08; A61G 13/104; A61G 13/121; A61G 13/122; A61G 13/123; A61G 13/1235; A61G 13/02; A61G 13/101; A61G 13/1205; A61G 7/001; A61G 7/002; A61G 7/005; A61G 7/008; A61N 5/1049; A61N 2005/105; A61N 2005/1061; A61N 5/107; A61N 5/1083; A61N 2005/1052; A61N 2005/1062; A61N 5/1067
USPC .............................. 378/4, 9, 19, 20, 193–197
See application file for complete search history.

(56) References Cited

U.S. PATENT DOCUMENTS 7,695,192 B2 * 4/2010 Henderson ............. A61B 6/037
378/198

2005/0234327 A1 * 10/2005 Saracen ............... A61B 6/0457
600/407
2009/0074151 A1 * 3/2009 Henderson ............. A61B 6/037
378/198

FOREIGN PATENT DOCUMENTS

| DE | 102005014188 A1 | 10/2006 | | |
|---|---|---|---|---|
| DE | 102008032294 A1 | 1/2010 | | |
| DE | 102009041172 A1 | 3/2011 | | |
| DE | 102011006122 A1 * | 9/2012 | ............ | A61B 6/4014 |
| JP | 2000116631 A | 4/2000 | | |
| JP | 200324314 A | 1/2003 | | |
| JP | 2006130159 A | 5/2006 | | |
| JP | 2006334020 A | 12/2006 | | |
| JP | 2010184037 A | 8/2010 | | |

OTHER PUBLICATIONS

German Patent Office; Search Report in German Patent Application No. 10 2013 226 289.2 dated Jul. 24, 2014; 7 pages.
Korean Patent Office; Office Action in Korean Patent Application No. 10 2016-7016261 dated Jun. 12, 2017; 15 pages.
Chinese Patent Office; Office Action in related Chinese Patent Application No. 2014800679114 dated Mar. 28, 2018; 16 pages.

* cited by examiner

X-RAY DEVICE HAVING AN ADJUSTING APPARATUS

TECHNICAL FIELD

The invention relates to an X-ray arrangement for a medical work station, having a particularly C-arm-shaped frame, which comprises a first frame section at which an X-ray transmitter is held and a second frame section opposite the first frame section at which an X-ray receiver is held.

BACKGROUND

DE 101 08 633 A1 describes an X-ray system for recording X-ray data-sets of patients. Among other things, mobile arc-shaped X-ray devices are used for medical and/or surgical interventions on a patient, by which parts of the patient's body can be recorded by X-ray imagery. This recording can yield three-dimensional X-ray images which are displayed on a monitor.

DE 101 11 798 A1 discloses a C-arm-shaped X-ray device, which includes a mobile cart on wheels. A lifting device with a column is disposed inside a housing of the C-arm X-ray device. A fastening part is arranged on the column, which in turn includes a bearing part to support a carrying device designed like a C-arm. The C-arm includes an X-ray radiation source and an X-ray image amplifier, which are arranged opposite each other on the C-arm such that a central beam originating in the X-ray radiation source impinges on the detector area of the X-ray image amplifier almost in the center. The C-arm is supported on the frame to be movable along its perimeter, i.e. rotationally, allowing both the X-ray radiation source as well as the X-ray image amplifier to perform a common orbital motion, in which the X-ray radiation source and the X-ray image amplifier remain unchanged with regards to their relative distance and their relative orientation.

The object of the invention is to provide an X-ray arrangement that can be used in a flexible fashion, particularly having an expanded range of operation.

SUMMARY

This object is achieved, according to the invention, in an X-ray arrangement for a medical work station, having a particularly C-arm-shaped frame, which comprises a first frame section at which an X-ray transmitter is held and a second frame section opposite the first frame section at which an X-ray receiver is held, furthermore comprising an adjustment device, which is designed to allow changing a relative pose of the X-ray transmitter and/or the X-ray receiver in reference to the C-arm-shaped frame by adjusting the pose of the X-ray transmitter at the first frame section and/or by adjusting the pose of the X-ray receiver at the second frame section independent of each other.

Here, pose is to be understood as the sum of three positions and three orientations of an object in the space. To this regard, the relative pose of the X-ray transmitter in reference to the C-arm-shaped frame represents the relative position and orientation, i.e. the position and orientation of the X-ray transmitter in reference to the C-arm-shaped frame. Similarly, the relative pose of the X-ray receiver in reference to the C-arm-shaped frame represents the relative position and orientation, i.e. the position and orientation of the X-ray receiver in reference to the C-arm-shaped frame. Any adjustment of the pose of the X-ray transmitter at the first frame section therefore leads to an adjustment of the position and orientation, i.e. the position and orientation of the X-ray transmitter, in reference to the first frame section. An adjustment of the pose of the X-ray receiver at the second frame section therefore leads to an adjustment of the position and orientation, i.e. the position and orientation of the X-ray receiver, in reference to the second frame section.

The fact that adjusting the pose of the X-ray receiver and/or the X-ray transmitter occurs independently of each other, entails, among other things, that, for example, the mutual orientation of X-ray receiver and X-ray transmitter can be changed, that at the same time the distance from the X-ray receiver to the X-ray transmitter can be changed, and that, optionally, the X-ray receiver and/or the X-ray transmitter can be adjusted in different or identical directions in relation to the C-arm-shaped frame. In particular, tilting and/or inclining the X-ray receiver and/or the X-ray transmitter become possible.

In a first embodiment, the adjustment device may comprise a joint arranged between the first frame section and the X-ray transmitter, adjustably connecting the X-ray transmitter with the C-arm-shaped frame and having at least one degree of freedom. This embodiment of an adjustment device can be used to move, particularly adjust, the X-ray transmitter in reference to the C-arm-shaped frame and simultaneously also in reference to the X-ray receiver. In another, further developed embodiment, the X-ray receiver can additionally be moved and/or adjusted, independent of any adjustment of the X-ray transmitter. The adjustment device can particularly be configured to move or swivel the X-ray transmitter in at least one further degree of freedom, i.e. to tilt or incline it, in addition to moving it in the direction of the connecting line from the X-ray transmitter to the X-ray receiver, and in addition to rotating it about the connecting lineline, move it. In a special embodiment, the adjustment device may have a sufficient number of degrees of freedom, allowing to move the X-ray transmitter in a predetermined 3D-volume, particularly in a stepless fashion, along any desired paths and/or rotate it about any desired axes.

In a second embodiment, alternative or complementary to the first embodiment, the adjustment device may comprise a joint with at least one degree of freedom, arranged between the second frame section and the X-ray receiver, adjustably connecting the X-ray receiver with the C-arm-shaped frame. This embodiment of an adjustment device can be used to move, particularly adjust, the X-ray receiver in reference to the C-arm-shaped frame and simultaneously also in reference to the X-ray transmitter. In a further embodiment, the X-ray transmitter can also be moved and/or adjusted independent of an adjustment of the X-ray receiver. The adjustment device can particularly be configured such that, in addition to moving it in the direction of the connecting line of the X-ray transmitter and the X-ray receiver and in addition to rotating it about said connecting line, it can linearly move or swivel the X-ray receiver also in at least one other degree of freedom, i.e. to tilt it or to incline it. In a special embodiment, the adjustment device may have a sufficient number of degrees of freedom, by which it is possible to move the X-ray receiver in a predetermined 3D-volume, particularly in a stepless fashion, along any desired paths, and/or to rotate them about any desired axes.

In one variant the link may generally include a linear guide for the translational movement of the X-ray transmitter and/or the X-ray receiver, particularly a linear drive automatically adjusted by way of a motor. In a simple case, the linear guide may represent a rail, which is fastened at the first and/or second frame section and on which the X-ray transmitter and/or the X-ray receiver can be adjusted like a sled on a fixed predetermined straight path. The linear drive may include such a linear guide or rail, wherein additionally a motor is provided in order to actively move the X-ray transmitter and/or the X-ray receiver, particularly in an automatically controlled fashion. The motor may be an electric motor, for example, with its motor shaft being connected to a spindle, which converts the rotary motion of the electric motor into a linear motion of the X-ray transmitter and/or the X-ray receiver.

The linear guide, particularly the linear drive that can be automatically adjusted via a motor, can here be designed to move the X-ray transmitter and/or the X-ray receiver in a direction extending perpendicular to the plane of the C-arm-shaped frame. The X-ray transmitter and/or the X-ray receiver can be moved parallel to the rotary axis, which extends through the center of the C-arm-shaped frame, out of the plane of said C-arm-shaped frame. If both the X-ray transmitter and the X-ray receiver are simultaneously moved in a direction extending perpendicular to the plane of the C-arm-shaped frame, such a motion can avoid or reduce an otherwise required translational displacement of the entire X-ray device. This results in an enlargement of the working space of the X-ray system. This can be particularly beneficial in the environment of a medical work station, in which only little space is available for the movement of large machinery.

The linear guide, particularly the linear drive that can automatically be adjusted via a motor, can here be designed such that the X-ray transmitter and/or the X-ray receiver move in the direction of a connecting line from the X-ray transmitter to the X-ray receiver. The X-ray transmitter and the X-ray receiver can be moved towards and from each other by moving the X-ray transmitter and/or the X-ray receiver in the direction of the connecting line from the X-ray transmitter to the X-ray receiver via such an adjustment device.

The linear guide, particularly the linear drive that can be automatically adjusted by a motor, can here be designed to move the X-ray transmitter and/or the X-ray receiver in the plane of the C-arm-shaped frame perpendicular to the connecting line from the X-ray transmitter to the X-ray receiver. In other words, the X-ray transmitter and/or the X-ray receiver can be moved tangentially or along a secant or a passant in reference to the C-arm-shaped frame.

In another variant, alternative or complementary to the translational motion, the joint may generally include a pivot bearing for the rotational movement of the X-ray transmitter and/or the X-ray receiver, particularly a rotary drive that can be automatically adjusted by a motor. Here, a motor may be provided in order to actively move the X-ray transmitter and/or the X-ray receiver, particularly in an automatically controlled fashion. The motor can for example be an electric motor, with its motor shaft being connected to the X-ray transmitter and/or the X-ray receiver in order to rotate them in the desired orientation. The motor shaft may here be coupled directly to the X-ray transmitter or the X-ray receiver. Alternatively, the motor shaft can be connected to a transmission, which in turn on the transmission output side is connected to the X-ray transmitter or the X-ray receiver.

The pivot bearing, particularly a rotary drive automatically adjusted by a motor, can here be designed to rotate the X-ray transmitter and/or the X-ray receiver about an axis extending perpendicular to the plane of the C-arm-shaped frame. In this respect, a rotation or pivoting of the X-ray transmitter and/or the X-ray receiver can be achieved within the plane of the C-arm-shaped frame.

The pivot bearing, particularly the rotary drive that can be automatically adjusted by a motor, can be embodied such that the X-ray transmitter and/or the X-ray receiver rotate about an axis extending parallel to the connecting straight, particularly along the connecting straight from the X-ray transmitter to the X-ray receiver. By rotating the X-ray transmitter and/or the X-ray receiver about an axis, extending parallel in reference to the connecting straight, particularly along the connecting straight from the X-ray transmitter to the X-ray receiver, here the X-ray transmitter can be quasi distorted in reference to the X-ray receiver.

The pivot bearing, particularly the rotary drive that can be automatically adjusted by a motor, may be designed to rotate the X-ray transmitter and/or the X-ray receiver about an axis positioned in the plane of the C-arm-shaped frame and extending perpendicular to the connecting line from the X-ray transmitter to the X-ray receiver. By rotating the X-ray transmitter and/or the X-ray receiver about an axis located in the plane of the C-arm-shaped frame and extending perpendicular to the connecting line from the X-ray transmitter to the X-ray receiver, the X-ray transmitter and/or the X-ray receiver can be pivoted in reference to the C-arm-shaped frame. Pivoting may be beneficial, for example, if the X-ray device per se is not to be moved away from the medical work station, but the area of operation is to be made more accessible for a brief period of time. A surgeon can so for example pivot the X-ray transmitter and/or the X-ray receiver out of his/her visual range without having to move the C-arm-shaped frame; this can particularly apply to the kinematic configuration using the linear guides, since they allow movement of the interference contours.

In all embodiments of the X-ray device, the adjustment device, particularly the joint or the plurality of joints, may be designed in general to move the X-ray transmitter and/or the X-ray receiver independent of each other in reference to each other.

The adjustment device, particularly the joint or the plurality of joints, may generally be designed as a serial kinematic configuration of the type of a horizontal jointed-arm robot, particularly a SCARA-robot with particularly at least four degrees of freedom, particularly three rotational degrees of freedom and optionally one translational degree of freedom. Among the four degrees of freedom, three of them may represent rotational degrees of freedom, with the fourth degree of freedom representing a linear motion. The fourth degree of freedom executing a linear motion may optionally be omitted.

A first joint of the serial kinematic configuration, particularly the jointed-arm robot and/or the SCARA-robot, may include an annular first link, which is fastened particularly to the C-arm-shaped frame, in which an annular disk-shaped second link is coaxially pivoted in reference to the first link, and a second joint, directly abutting the first joint in a serial kinematic chain, includes an annular disk-shaped third link, which is pivoted eccentrically in the annular disk-shaped second joint. Thus, in this embodiment both the joint arranged between the first link and the second link as well as the abutting joint arranged between the second link and the third link are designed as swivel joints. Both swivel joints show axes of rotation aligned parallel to each other. Due to the ring-shaped and/or annular disk-shaped body of the links, the two joints are arranged in a so-called nested fashion, wherein the combination of joints has a large diameter but a relatively low structural height, which considerably differs from SCARA kinematic configurations previously known to a person skilled in the art. Such a flat design also results in a very stiff and space-saving construction in the direction of the rotational. The stiff construction also relates to the other joint with which the transmitter and/or the receiver can be rotated. A particular stiffness in the system also results from the lever arms and the drive stiffness, particularly of the linear axis of the SCARA kinematic configuration.

A resulting advantage can be, for example, that the mechanism does not assume a shape, i.e. an interfering contour, which could represent a risk of colliding with the C-arm-shaped frame in the case of a reconfiguration of the position of the X-ray transmitter and/or the X-ray receiver. Reorientation does not lead to any change of the exterior contour of the mechanism of the first two joints. The mechanism is therefore designed such that the retention forces for the X-ray transmitter and/or the X-ray receiver, in the plane in which they can be moved, are not absorbed by the drives of the joints but rather by the bearings of the joints, and via them passed on to the frame structure. This can lead to energy savings and/or improved path accuracy, which is particularly beneficial for imaging processes. The mechanism is designed such that it is stiffer than other mechanisms used in robots, which additionally benefits imaging methods.

In a concrete embodiment of the serial kinematic configuration, the first link comprises an annular body connected fixed to the C-arm-shaped frame, particularly to the first or second frame section. The annular body has a diameter that is considerably larger than its structural height. Inside the annular body, coaxial with the annular body, an annular disk-shaped body is pivoted coaxial with the central axis of the annular body. The annular disk-shaped body particularly has a structural height which is not greater than the structural height of the annular body. The annular disk-shaped body can for example be pivoted in the annular body by means of at least one roller bearing. The annular disk-shaped body and the annular body thus form a first pivot joint of the serial kinematic configuration.

The annular disk-shaped body comprises a circular recess. A second annular disk-shaped body is pivoted in this circular recess, having a smaller diameter and adjusted to said circular recess. The second annular disk-shaped body particularly has a structural height which is not greater than the structural height of the first annular disk-shaped body. The second annular disk-shaped body can also be eccentrically pivoted on the first annular disk-shaped body by means of a roller bearing. The second annular disk-shaped body and the first annular disk-shaped body thus form a second pivot joint of the serial kinematic configuration.

A push rod which longitudinally extends perpendicular to the plane in which the two annular disk-shaped bodies and the annular body are located is movably supported on the second annular disk-shaped body. The push rod is supported in a translational adjustable fashion via a linear guide or a linear drive. For this purpose, the push rod may for example comprise a spindle which can in particular be automatically driven by an electromotive drive. The second annular disk-shaped body and the push rod form a third joint of the serial kinematic configuration, namely a prismatic joint.

The prismatic joint or the push rod itself may be additionally pivoted at the second annular disk-shaped body, particularly about an axis perpendicular to the plane in which the two annular disk-shaped bodies and the annular body are located. The prismatic joint or the push rod is pivoted to be rotatable about the direction in which the prismatic joint or the push rod is supported for translational movement. The prismatic joint that can be pivoted in relation to the second annular disk-shaped body or the push rod that can be pivoted in relation to the second disk-shaped body and the annular disk-shaped body form a fourth joint of the serial kinematic configuration, namely another pivot joint.

Either the X-ray transmitter or the X-ray receiver is therefore held adjustably with respect to its respective pose in relation to the frame section and/or the C-arm-shaped frame on a free end of the articulate prismatic joint and/or on a free end of the push rod.

In case the adjustment device, particularly the joint or the plurality of joints, is designed as a serial kinematic configuration of the type of a horizontal jointed-arm robot, generally at least one joint, particularly several joints or all joints of the horizontal jointed-arm robot, particularly the SCARA robot together with the associated X-ray transmitter or X-ray receiver, can be designed in a gravity compensating manner.

In a special embodiment, which includes an annular body as a first link, a first and a second annular disk-shaped body as the second and third links, gravity can be compensated for by disposing a compensation weight both on the first as well as on the second annular disk-shaped body. A compensation weight fastened to the second annular disk-shaped body compensates essentially for the weight of the X-ray transmitter or the X-ray receiver and the weight of the prismatic joint and/or the push rod. The compensation weight fastened to the first annular disk-shaped body compensates essentially for the weight of the X-ray transmitter or the X-ray receiver, the weight of the prismatic joint and/or the push rod, and the weight of the second annular disk-shaped body. As a result, the center of gravity of the annular disks is always in their center, regardless of the rotational position of the joints.

Rotation of the C-arm within the earth's gravity field applies no variable forces to the mechanism. This may have the advantage that only the dynamic forces must be applied by the drives of the mechanism. This is further advantageous in that smaller motors can be selected than required in classic SCARA kinematics, wherein motors need to compensate gravity in case of any rotation of the C-arm. Furthermore, it may be advantageous that the mechanism may not require any additional brakes to avoid a change of position, e.g. due to loss of power. Furthermore, it may be advantageous that gravity has no influence on positioning and/or path accuracy. The kinematic configuration of the drive trains can be selected such that they apply a brake torque which ensures secure fastening of the X-ray system even during a rotation of the C-arm-shaped frame. Furthermore, the drive may be designed such that it can be operated inversely, which allows manual operation of the X-ray system based on the joint kinematics of the pivot joints even in case of power outages.

In all embodiments the X-ray device, particularly the X-ray transmitter and/or the X-ray receiver, can include manual operating means for the manual or partially automated movement of the X-ray transmitter and/or X-ray receiver in reference to the C-arm-shaped frame.

In a first variant of the operating means the force applied from outside to a sensor is detected by force sensors in the drive train or by current measurements at the motors. This is particularly possible for drives of the two rotary motions of the serial kinematic configuration because the forces applied act directly upon the motors and drive trains. Excluded are the stretch positions of the kinematic configuration in which the forces are not absorbed by the motors but by the support structure. Due to the fact that the degree of freedom for lifting the sensor has a large transmission ratio, any measurement of force on the drive side will be rather difficult. Force measurement on the driven side is more precise for this degree of freedom.

An overall easier solution results therefore from another variant of an operating means, when sensors are attached to the X-ray transmitter and/or the X-ray receiver which a user can use to push the X-ray transmitter and/or the X-ray receiver away. These sensors detect the force transmitted by the hand of the user in terms of strength and direction. This has an additional technical safety effect, because the X-ray transmitter and/or the X-ray receiver can only be moved by touching the sensor. In order to support this aspect, such manual movement can only be activated by pressing a consent button.

In summary, the invention results in an advantageous fastening of a mechanism which includes a Scara-kinematic configuration consisting of three nested rotary cylinders which house a linear motion, resulting in an improved medical device. The medical device can comprise a C-arm to which the mechanism is attached. The medical device can for example be used for angiography.

The mechanism can be designed such that, for example, planar Scara motions are independent of the position and orientation of the field of gravity, i.e. of a movement of the C-arm. This occurs by a shift of the respective centers of gravity into the center of the three axes of rotation. This results in that only the dynamic forces need to be applied for driving the mechanism. Furthermore, gravity has no effects on positioning and path accuracy.

The mechanism can be designed such that no additional brakes are required in order to avoid a change in position due to loss of power.

The mechanism can be designed such that it does not assume a shape which could represent a risk of colliding with the moving C-arm when the position of the receiver is changed. The exterior shape of the eccentrically nested disks does not change during a change in position of the receiver.

The mechanism can also be designed such that the retention forces for the receiver in the plane in which it can be moved are not absorbed by the drives of the joints but by the bearings of said joints, and transferred by them to the support structure. This can lead to energy savings and improved path accuracy in motion, which is particularly beneficial for imaging methods.

The support properties allow a stiff design of the mechanism, which benefits imaging processes.

BRIEF DESCRIPTION OF THE DRAWINGS

Several concrete exemplary embodiments of various inventive X-ray devices are explained in greater detail in the following description with reference to the attached figures. Concrete features of these exemplary embodiments may represent general features of the invention, regardless of the context in which they are mentioned, viewed either individually or in combinations.

Wherein.

DETAILED DESCRIPTION

Figure 1:
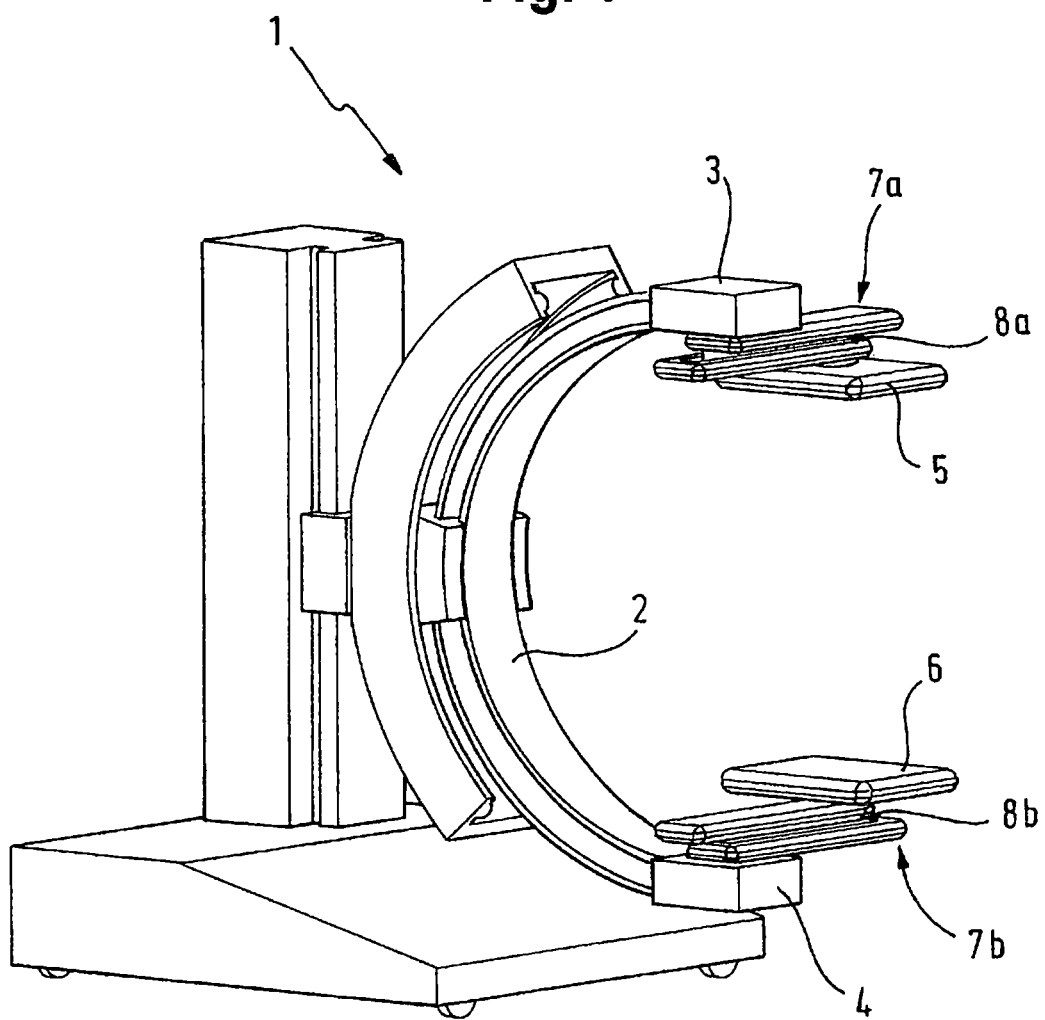
FIG. 1 shows an exemplary X-ray arrangement with a first embodiment of an adjustment device on an X-ray transmitter and an X-ray receiver with a linear guide.

FIG. 1 shows an X-ray arrangement 1. The X-ray arrangement 1 in the exemplary embodiment includes a C-arm-shaped frame 2, which is dually supported in a circular guide. The C-arm-shaped frame 2 comprises a first frame section 3 to which an X-ray transmitter 5 is fastened. The C-arm-shaped frame 2 comprises another, second frame section 4 opposite the first frame section 3 to which an X-ray receiver 6 is fastened. In the exemplary embodiment shown here, the first frame section 3 comprises a first adjustment device 7a and the second frame section 4 comprises a second adjustment device 7b.

Each adjustment device 7a, 7b is configured to change a relative pose of the X-ray transmitter 5 and/or the X-ray receiver 6 in reference to the C-arm-shaped frame 2 by adjusting the pose of the X-ray transmitter 5 on the first frame section 3 and/or by adjusting the pose of the X-ray receiver 6 on the second frame section 4 independently of each other.

One adjustment device 7a includes a joint 8a arranged between the first frame section 3 and the X-ray transmitter 5, adjustably connecting the X-ray transmitter 5 to the C-arm-shaped frame 2, with at least one degree of freedom.

The other adjustment device 7b includes a joint 8b, arranged between the second frame section 4 and the X-ray receiver 6 and adjustably connecting the X-ray receiver 6 to the C-arm-shaped frame 2, provided with at least one degree of freedom.

Figure 2:
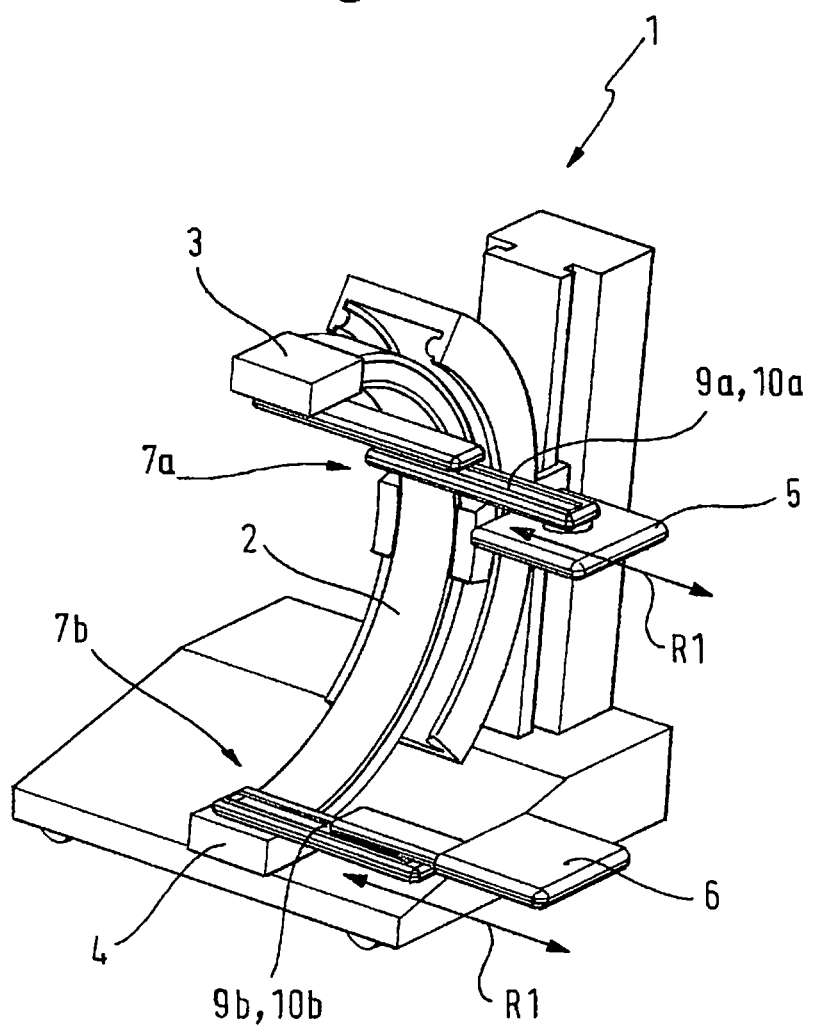
FIG. 2 shows the X-ray arrangement according to FIG. 1 with a linearly extended X-ray transmitter and X-ray receiver in a direction extending perpendicular to the plane of the C-arm-shaped frame.

In the exemplary embodiment of FIG. 1 the joints 8a, 8b are configured for the translational movement of the X-ray transmitter 5 and/or the X-ray receiver 6 and each comprise, as is clearly visible in FIG. 2, a linear guide 9a, 9b, particularly a linear drive 10a, 10b, that can be automatically adjusted by a motor.

The linear guides 9a, 9b, particularly the linear drives 10a, 10b that can be automatically moved by motors not shown in greater detail, are designed to move the X-ray transmitter 5 and/or the X-ray receiver 6 in a direction R1 extending perpendicular to the plane of the C-arm-shaped frame.

FIG. 2 also shows how the linear guides 9a, 9b, particularly the linear drives 10a, 10b can be configured to move both the X-ray transmitter 5 and the X-ray receiver 6 simultaneously, particularly synchronously, in the direction R1.

The linear guides 9a, 9b, as shown in FIG. 2, can in a simple case be rails which are fastened to the first frame section 3 and/or to the second frame section 4 and on which the X-ray transmitter 5 and/or the X-ray receiver 6 can be adjusted along a fixed predetermined straight path like a sled.

If both the X-ray transmitter 5 as well as the X-ray receiver 6 are moved simultaneously in a direction R1 extending perpendicular to the plane of the C-arm-shaped frame 2, as shown in FIG. 2, an otherwise required translational movement of the entire X-ray arrangement 1 can be optionally avoided or reduced.

Figure 3:
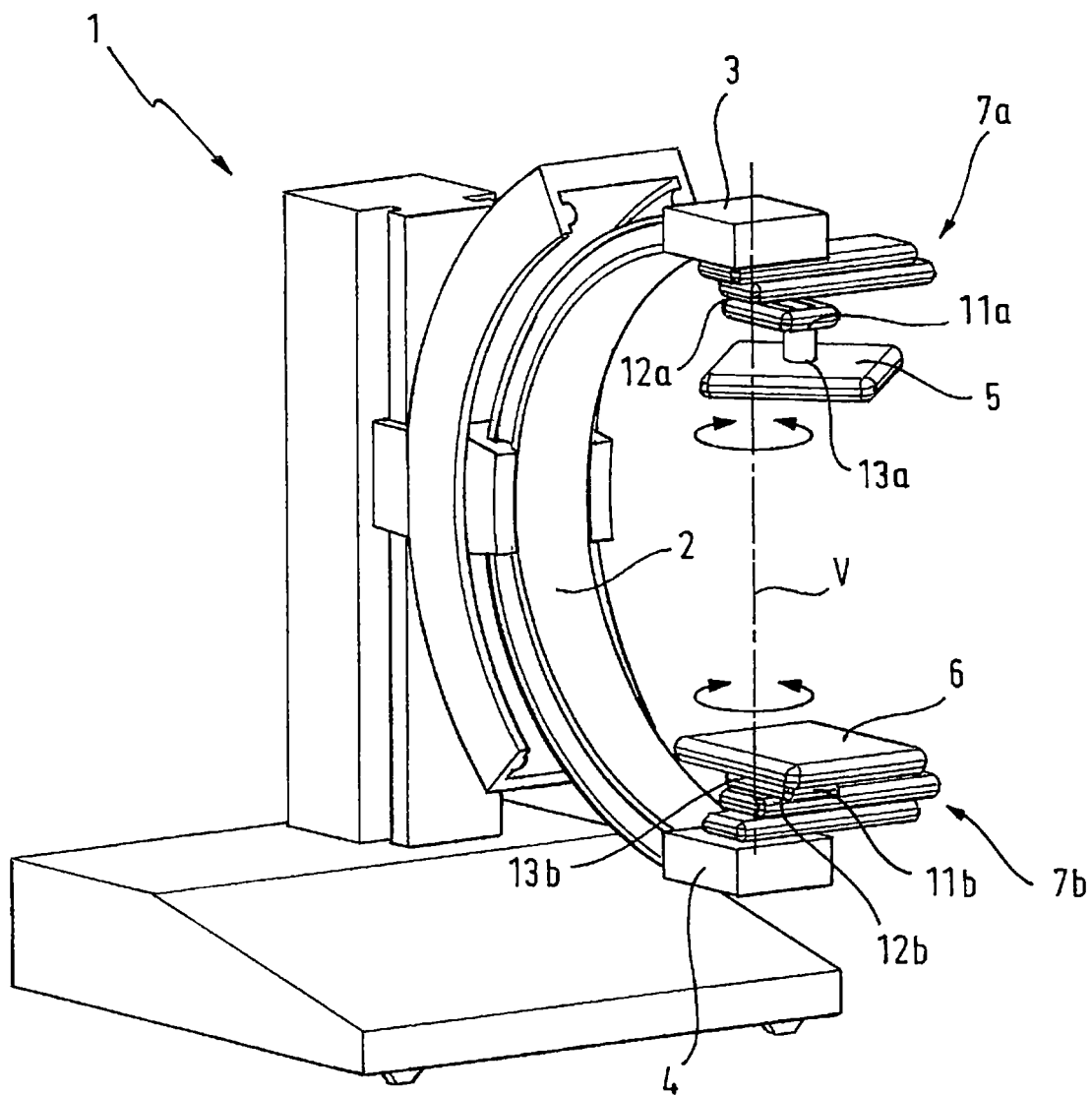
FIG. 3 shows an exemplary X-ray arrangement in a variant of the adjustment device with a pivot joint, which is designed to rotate the X-ray transmitter and the X-ray receiver about an axis extending parallel to the connecting line, particularly along the connecting line from the X-ray transmitter to the X-ray receiver.

FIG. 3 shows an alternative and/or complementary exemplary embodiment of an X-ray arrangement 1, in which at least one additional joint 11a, 11b is provided for the rotational movement of the X-ray transmitter 5 and/or the X-ray receiver 6, shown here are two of them, comprising pivot bearings 12a, 12b, 13a, 13b.

The pivot bearings 12a, 12b, 13a, 13b are configured to rotate the X-ray transmitter 5 and/or the X-ray receiver 6 about an axis extending parallel to the connecting line V, particularly along the connecting line V from the X-ray transmitter 5 to the X-ray receiver 6.

Figure 4:
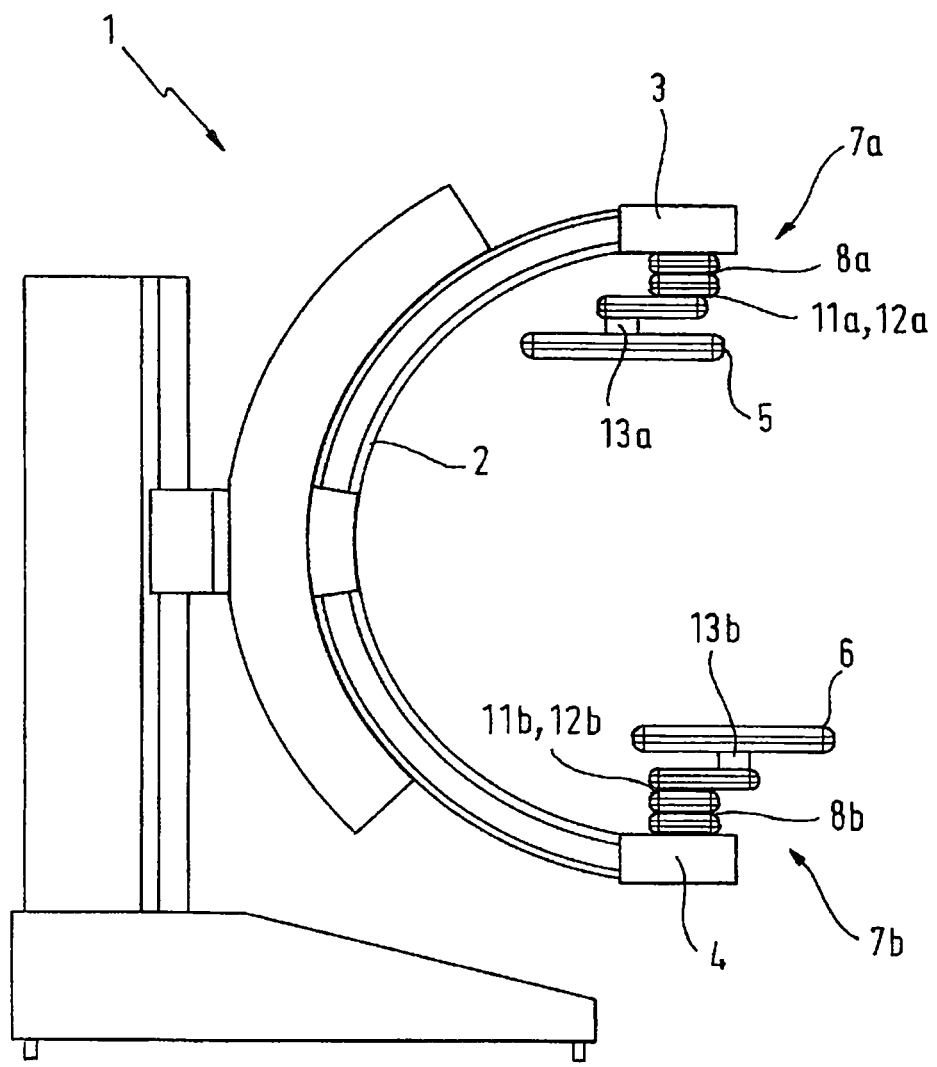
FIG. 4 shows an exemplary X-ray arrangement in another variant of the adjustment device with a linear guide, which is designed to move the X-ray transmitter and the X-ray receiver in the plane of the C-arm-shaped frame perpendicular to the connecting line from the X-ray transmitter to the X-ray receiver.

FIG. 4 indicates how lateral, mutually opposite adjustment of the X-ray transmitter 5 and the X-ray receiver 6 can be achieved by a suitable rotation of both the pivot bearing 12a, 12b as well as the pivot bearing 13a, 13b.

Figure 5:
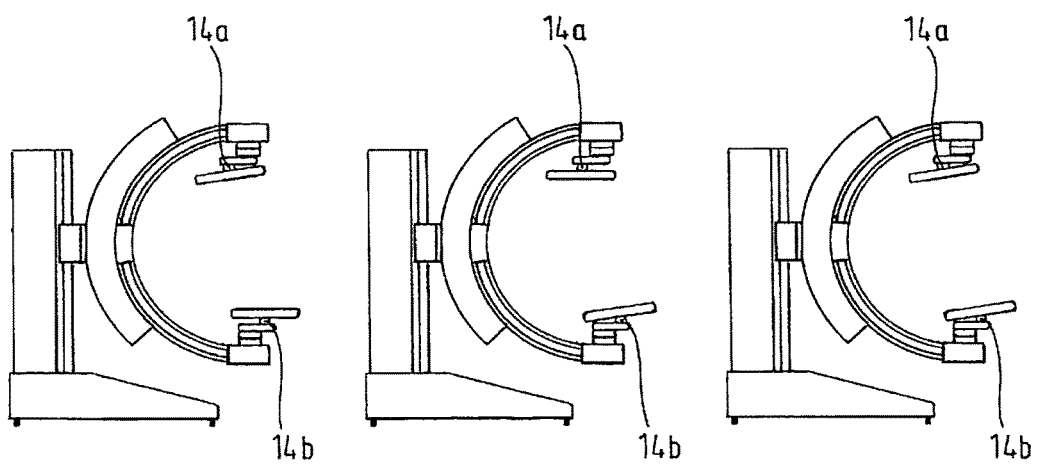
FIG. 5 shows an exemplary X-ray arrangement in another variant of the adjustment device with a pivot joint designed to tilt and/or incline the X-ray transmitter and/or the X-ray receiver.

In an alternative embodiment of pivot joints 11a, 11b, according to FIG. 5, the pivot bearings 14a, 14b are designed to rotate the X-ray transmitter 5 and/or the X-ray receiver 6 about an axis extending perpendicular to the plane of the C-arm-shaped frame 2, that is, perpendicularly out of the drawing plane, i.e. to tilt or incline them.

Figure 6:
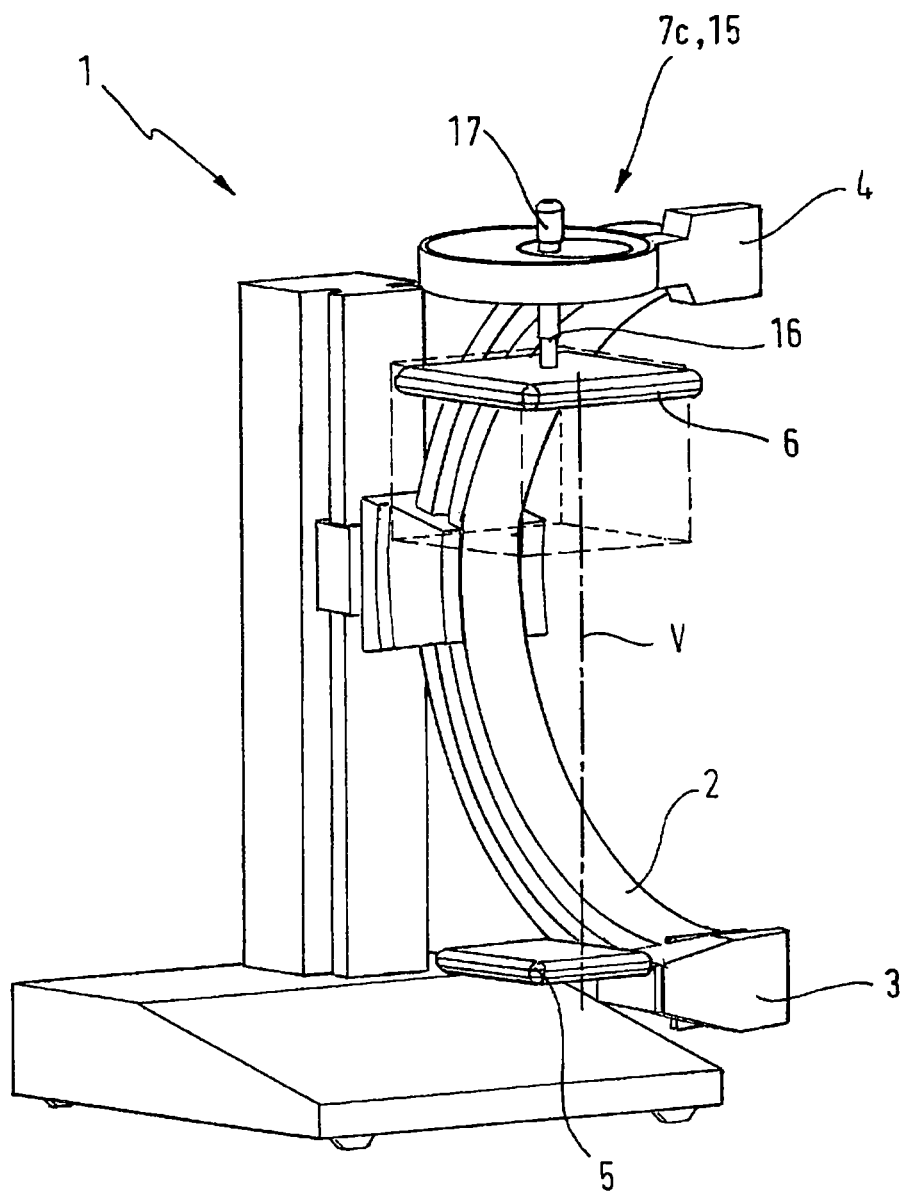
FIG. 6 shows an exemplary X-ray arrangement with an alternative embodiment of an adjustment device, which is designed as a serial kinematic configuration like a horizontal jointed-arm robot, particularly a SCARA-robot with four degrees of freedom.

FIG. 6 shows a particular embodiment of an adjustment device 7c, which is embodied as a serial kinematic configuration 15 like a horizontal jointed-arm robot, particularly a SCARA-robot, with at least four degrees of freedom.

Such a serial kinematic configuration 15 like a SCARA-robot comprises as a special feature a pivot bearing 16, by which for example the X-ray receiver 6 can be rotated about an axis extending parallel to the connecting line V from the X-ray transmitter 5 to the X-ray receiver 6.

Furthermore, the serial kinematic configuration 15 according to FIG. 6 includes a lifting device 17, forming a linear guide or a linear drive, which is configured as shown, for example, in FIG. 6, to move the X-ray receiver 6 in the direction of the connecting line V from the X-ray transmitter 5 to the X-ray receiver 6. The serial kinematic configuration 15 according to FIG. 6 is shown enlarged as an isolated part in FIG. 7. The serial kinematic configuration 15 comprises a first annular link 20a, in which an annular disk-shaped second link 21a is coaxially pivoted in reference to the first link 20a. The first link 20a and the second link 21a form a first joint 22a of the serial kinematic configuration 15. A second joint 23a, directly following the first joint 22a in a serial kinematic chain, comprises an annular disk-shaped third link 24a, which is eccentrically pivoted in the annular disk-shaped second link 21a.

In a concrete embodiment of the serial kinematic configuration 15 the first link 20a comprises an annular body 20, fixedly connected to the C-arm-shaped frame 2, particularly to the first frame section 3 or the second frame section 4. The annular body 20 has a diameter that is considerably larger than its structural height. Inside the annular body, coaxial with the annular body 20, an annular disk-shaped body 21 is pivoted coaxially with the central axis of the annular body 20. The annular disk-shaped body 21 particularly shows a structural height that is no higher than the structural height of the annular body 20. The annular disk-shaped body 21 can for example be pivotably supported in the annular body 20 by at least one roller bearing. The annular disk-shaped body 21 and the annular body 20 form here a first pivot joint (joint 22a) of the serial kinematic configuration 15.

The annular disk-shaped body 21 comprises a circular recess. In this circular recess a second annular disk-shaped body 24 is rotationally supported, which has a small diameter and is adjusted to the circular recess. The second annular disk-shaped body 24 in the exemplary embodiment illustrated has a structural height which is not greater than the structural height of the first annular disk-shaped body 21. In other embodiments, not shown in greater detail, the second annular disk-shaped body 24 may actually have a structural height greater than the structural height of the first annular disk-shaped body 21. The second annular disk-shaped body 24 can also be pivotably supported by a roller bearing at the first annular disk-shaped body 21. The second annular disk-shaped body 24 and the first annular disk-shaped body 21 form here a second pivot joint (joint 23a) of the serial kinematic configuration 15.

A push-rod 25 (lifting device 17) is movably supported on the second annular disk-shaped body 24 and extends longitudinally perpendicular to a plane in which the two annular disk-shaped bodies 21, 24 and the annular body 20 are located. The push rod 25 (lifting device 17) is supported by a linear guide or a linear drive in a translationally adjustable fashion. For this purpose, the push rod 25 (lifting device 17) includes for example a spindle, not shown in greater detail, which can be automatically driven, for example by an electromotive drive. The second annular disk-shaped body 24 and the push rod 25 (lifting device 17) form a third joint 26 of the serial kinematic configuration 15, namely a prismatic joint. The kinematic can be configured such that the prismatic joint is arranged as the last joint.

The prismatic joint or the push rod 25 (lifting device 17) itself can additionally be pivotably supported, particularly about an axis located perpendicular to the plane in which the two annular disk-shaped bodies 21, 24 and the annular body 20 are located on the second annular disk-shaped body 24. The prismatic joint or the push rod 25 (lifting device 17) is supported pivotably about the direction in which the prismatic joint or the push rod 25 (lifting device 17) is supported for translational movement. The prismatic joint that can be pivoted about the second annular disk-shaped body 24 or the push rod 25 (lifting device 17) that can be pivoted about the second annular disk-shaped body 24, and the second annular disk-shaped body 24 form a fourth joint 27 of the serial kinematic configuration 15, namely another pivot joint 28.

Either the X-ray transmitter 5 or the X-ray receiver 6 is therefore held adjustably with respect to its respective pose in relation to the frame section 3, 4 and/or the C-arm-shaped frame 2 on a free end of the articulate prismatic joint and/or on a free end of the push rod 25 (lifting device 17).

Figure 7:
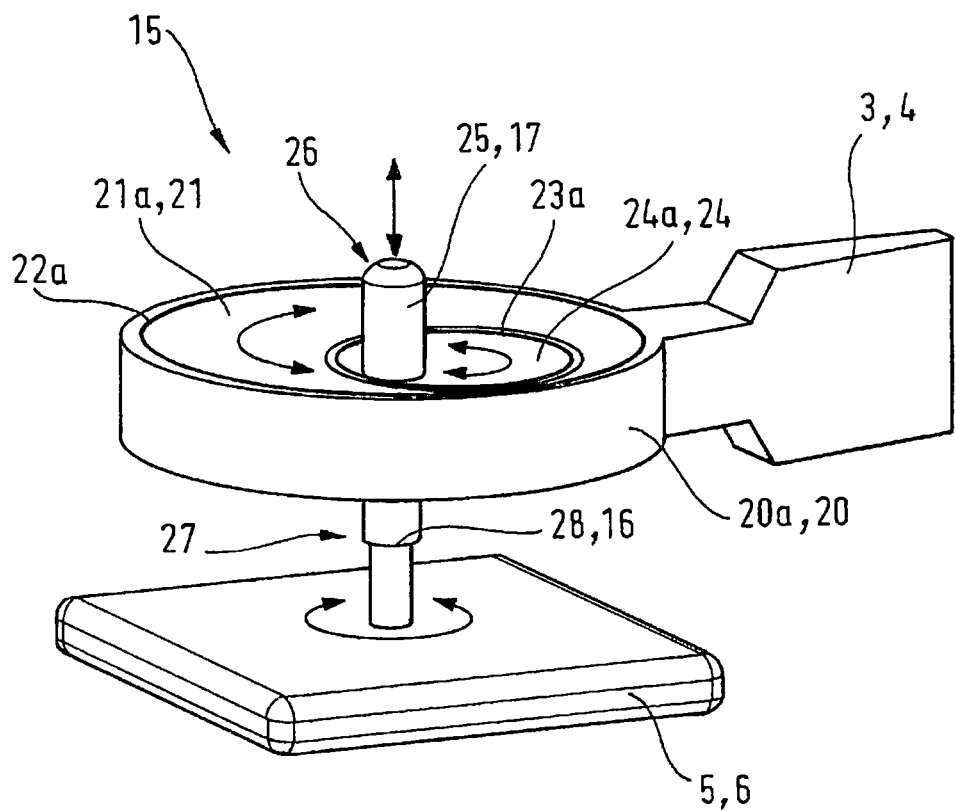
FIG. 7 shows an enlarged detail of the adjustment device designed like a horizontal jointed-arm robot according to FIG. 6.
Figure 8:
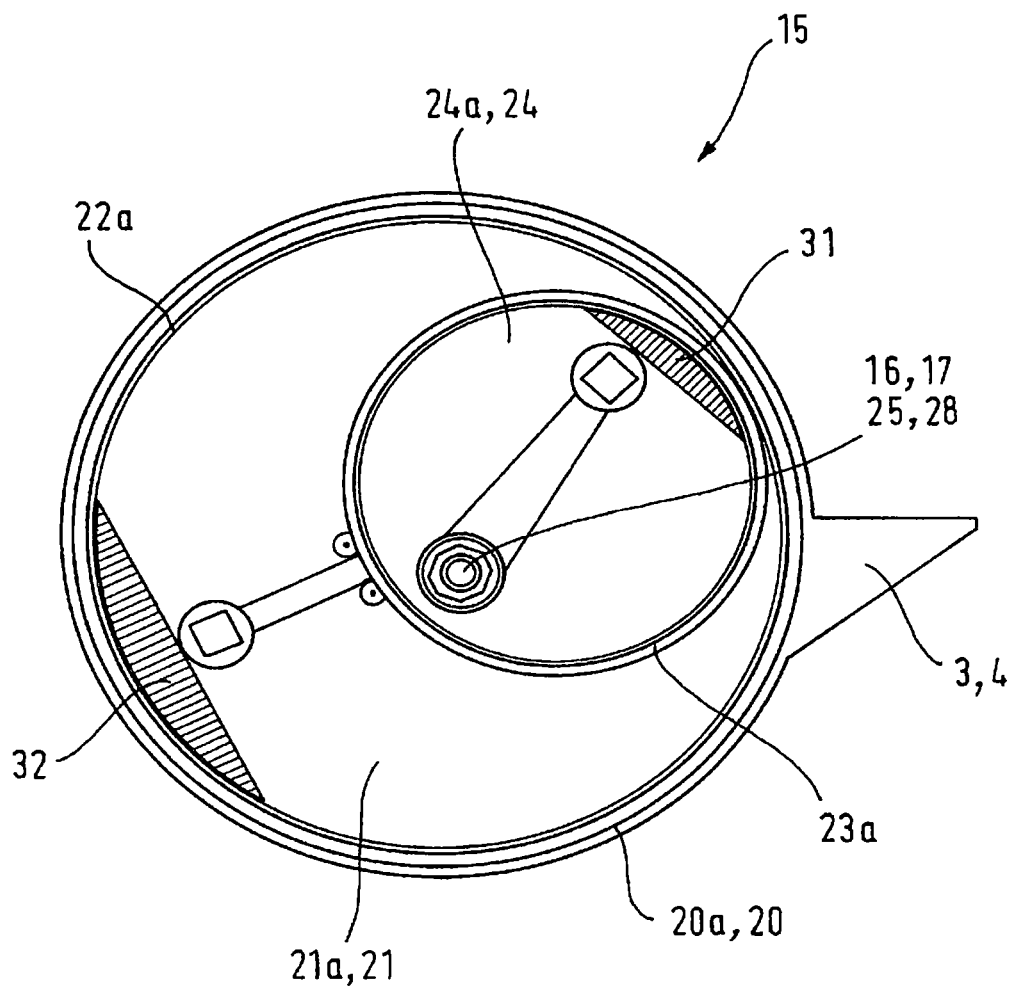
FIG. 8 is a schematic illustration of an adjustment device according to FIG. 7 with an annular first link, pivotably supporting an annular disk-shaped second link.

FIG. 8 schematically shows the serial kinematic configuration 15 according to FIG. 6 and FIG. 7, with a first compensation weight 31 and a second compensation weight 32 serving to compensate gravity.

In this embodiment shown in FIG. 8, which shows the annular body 20 as a first link 20a, shows the first annular disk-shaped body 21 as the second link 21a, and the second annular disk-shaped body 24 as the third link 24a, gravity can be compensated for by disposing the second compensation weight 32 to the first annular disk-shaped boy 21 and the first compensation weight 31 to the second annular disk-shaped body 24. The first compensation weight 31 fastened to the second annular disk-shaped body 24 compensates here essentially for the weight of the X-ray transmitter 5 or the X-ray receiver 6 and the weight of the prismatic joint and/or the push rod 25 (lifting device 17). The second compensation weight 32 fastened to the first annular disk-shaped body 21 essentially compensates for the weight of the X-ray transmitter 5 or the X-ray receiver 6, the weight of the prismatic joint or the push rod 25 (lifting device 17), and the weight of the second annular disk-shaped body 24.

Figure 9:
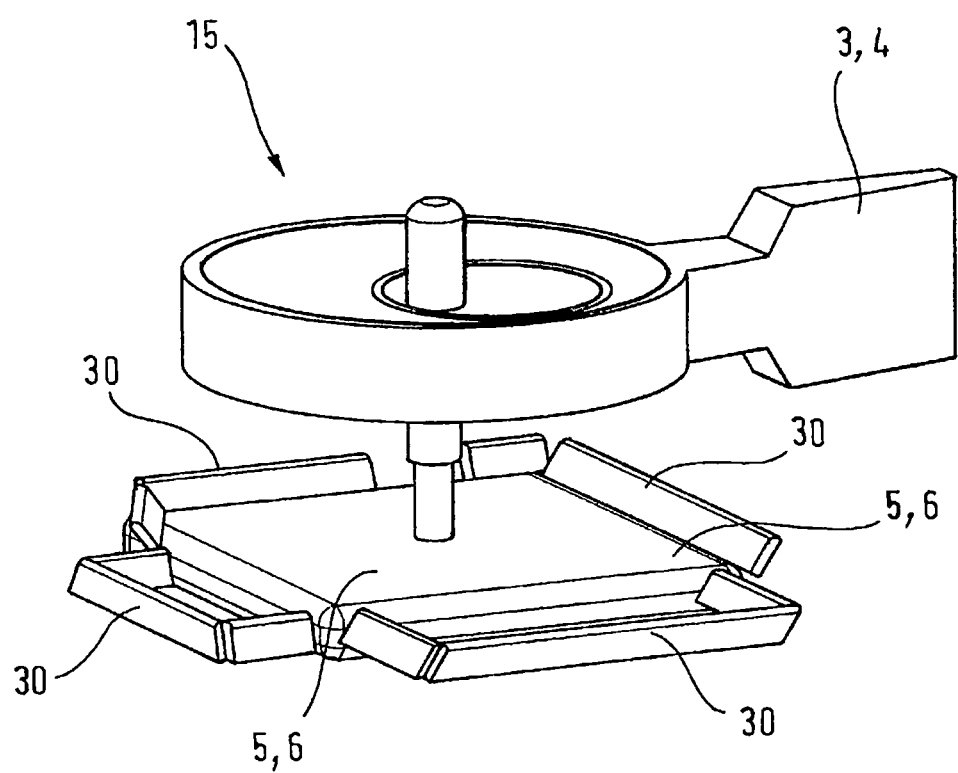
FIG. 9 is a schematic illustration of an operating means for the partially automated movement of the X-ray transmitter and/or the X-ray receiver.

FIG. 9 schematically shows manual operating means 30 for the manual or partially automated movement of the X-ray transmitter 5 and/or the X-ray receiver 6 in reference to the C-arm-shaped frame 2 and/or the frame section 3, 4.

Sensors, known in principle to a person skilled in the art, can be attached to the manual operating means 30, not shown in greater detail, which a user can use to push away the X-ray transmitter 5 and/or the X-ray receiver 6. Such sensors can for example detect the force in terms of strength and direction transmitted by the hand of the user. This has also a technical safety aspect, because the X-ray transmitter 5 and/or the X-ray receiver 6 can only be moved by touching the sensor. In order to support this aspect, such manual movement can only be activated by pressing a consent button, which is known to a person skilled in the art and not shown in greater detail.

While the present invention has been illustrated by a description of various embodiments, and while these embodiments have been described in considerable detail, it is not intended to restrict or in any way limit the scope of the appended claims to such detail. The various features shown and described herein may be used alone or in any combination. Additional advantages and modifications will readily appear to those skilled in the art. The invention in its broader aspects is therefore not limited to the specific details, representative apparatus and method, and illustrative example shown and described. Accordingly, departures may be made from such details without departing from the spirit and scope of the general inventive concept.

What is claimed is:

1. An X-ray arrangement for a medical work station, comprising:
    a frame having a first frame section supporting an X-ray transmitter, and having a second frame section opposite the first frame section and supporting an X-ray receiver; and
    an adjustment device configured to change the relative pose of the X-ray transmitter and/or the X-ray receiver relative to the frame by adjusting the pose of the X-ray transmitter at the first frame section and/or by adjusting the pose of the X-ray receiver at the second frame section, independently of one another;
    wherein the adjustment device is configured as a horizontal articulated arm robot with serial kinematics; and
    wherein the articulated arm robot comprises:
        a first joint comprising an annular first member and an annular disk-shaped second member coaxially and rotationally supported relative to the first member; and
        a second joint directly following the first joint in the serial kinematic chain, the second joint comprising an annular disk-shaped third member eccentrically arranged and rotationally supported in the annular disk-shaped second member of the first joint.

2. The X-ray arrangement of claim 1, wherein the frame is arc-shaped.

3. The X-ray arrangement of claim 2, further comprising manual operating means for the manual or partially automated movement of at least one of the X-ray transmitter or the X-ray receiver relative to the arc-shaped frame.

4. The X-ray arrangement of claim 3, wherein at least one of the X-ray transmitter or the X-ray receiver of the X-ray arrangement comprises the manual operating means.

5. The X-ray arrangement of claim 1, wherein the adjustment device includes at least one of:
    at least one adjustable first joint having at least one degree of freedom, the first joint arranged between the first frame section and the X-ray transmitter and adjustably connecting the X-ray transmitter to the frame; or
    at least one adjustable second joint having at least one degree of freedom, the second joint arranged between the second frame section and the X-ray receiver and adjustably connecting the X-ray receiver to the frame.

6. The X-ray arrangement of claim 5, wherein at least one of the first joint or the second joint comprises a linear guide that facilitates translational movement of at least one of the X-ray transmitter or the X-ray receiver.

7. The X-ray arrangement of claim 6, wherein the linear guide is a linear actuator.

8. The X-ray arrangement of claim 7, wherein the linear actuator is automatically adjustable via a motor.

9. The X-ray arrangement according to claim 6, wherein the frame is arc-shaped, and wherein at least one of:
    the linear guide is configured to move at least one of the X-ray transmitter or the X-ray receiver in a direction extending perpendicular to the plane of the arc-shaped frame;
    the linear guide is configured to move at least one of the X-ray transmitter or the X-ray receiver along a path collinear with a line extending between the X-ray transmitter and the X-ray receiver; or
    the linear guide is configured to move the at least one of the X-ray transmitter or the X-ray receiver in the plane of the arc-shaped frame, along directions perpendicular to the line extending between the X-ray transmitter and the X-ray receiver.

10. The X-ray arrangement according to claim 5, wherein at least one of the first joint or the second joint comprises a rotary bearing operable to rotationally move at least one of the X-ray transmitter or the X-ray receiver.

11. The X-ray arrangement of claim 10, wherein the rotary bearing comprises a rotary actuator.

12. The X-ray arrangement of claim 11, wherein the rotary actuator is automatically adjusted by a motor.

13. The X-ray arrangement of claim 10, wherein the frame is arc-shaped, and wherein at least one of:
    the rotary bearing rotates at least one of the X-ray transmitter or the X-ray receiver about an axis extending perpendicular to the plane of the arc-shaped frame;
    the rotary bearing rotates at least one of the X-ray transmitter or the X-ray receiver about an axis that is parallel to a line extending between the X-ray transmitter and the X-ray receiver; or the rotary bearing rotates at least one of the X-ray transmitter or the X-ray receiver about an axis extending in the plane of the arc-shaped frame and perpendicular to the line extending between the X-ray transmitter and the X-ray receiver.

14. The X-ray arrangement according to claim 1, wherein the adjustment device is a Selective Compliance Articulated Robot Arm (SCARA) robot with at least four degrees of freedom.

15. The X-ray arrangement according to claim 14, wherein the SCARA robot has three rotary degrees of freedom.

16. The X-ray arrangement according to claim 15, wherein the SCARA robot has one translational degree of freedom.

17. The X-ray arrangement of claim 1, wherein at least one joint of the horizontal articulated arm robot is coupled with the corresponding X-ray transmitter or the X-ray receiver in a gravity compensating manner.

* * * * *